United States Patent

Wagner et al.

[11] Patent Number: 5,929,119
[45] Date of Patent: Jul. 27, 1999

[54] FUNGICIDAL COMPOSITION

[75] Inventors: Oliver Wagner, Bexbach; Eberhard Ammermann, Heppenheim; Gisela Lorenz, Hambach, all of Germany

[73] Assignee: BASF Aktiengesellschaft, Ludwigshafen, Germany

[21] Appl. No.: 08/875,948

[22] PCT Filed: Jan. 30, 1996

[86] PCT No.: PCT/EP96/00349

§ 371 Date: Aug. 11, 1997

§ 102(e) Date: Aug. 11, 1997

[87] PCT Pub. No.: WO96/24249

PCT Pub. Date: Aug. 15, 1996

[30] Foreign Application Priority Data

Feb. 11, 1995 [DE] Germany ............... 195 04 599
Nov. 3, 1995 [DE] Germany ............... 195 40 970

[51] Int. Cl.⁶ .................................. A01N 37/18
[52] U.S. Cl. ............... 514/623; 514/613; 514/617; 514/618; 514/619; 514/622; 514/624; 514/625; 514/628; 514/629
[58] Field of Search ............... 514/613, 617, 514/618, 619, 623, 625, 628, 629, 622, 624

[56] References Cited

U.S. PATENT DOCUMENTS 4,666,943  5/1987  Noguchi et al. ............... 514/627
5,059,623  10/1991 Kruger et al. ............... 514/613
5,492,931  2/1996  Krueger et al. ............... 514/613

*Primary Examiner*—Allen J. Robinson
*Attorney, Agent, or Firm*—Oblon, Spivak, McClelland, Maier & Neustadt, P.C.

[57] ABSTRACT

A composition which is suitable for controlling fungal pests, comprising conventional additives and an effective amount of a p-hydroxyaniline derivative of the general formula I

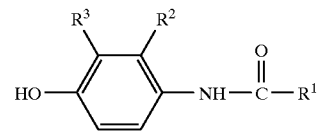

where the substituents have the following meanings:

$R^1$ is hydrogen, unsubstituted or substituted alkyl, unsubstituted or substituted bicycloalkyl, unsubstituted or substituted bicycloalkenyl;

$R^2$ and $R^3$ independently of one another are halogen, alkyl, haloalkyl, alkoxy or haloalkoxy, and a liquid or solid carrier, its use, the use of the compounds I for controlling fungal pests, and the use of the compounds I for the preparation of the compositions.

19 Claims, No Drawings

FUNGICIDAL COMPOSITION

This is a 371 of PCT/EP96/00349, filed Jan. 30, 1996

BACKGROUND OF THE INVENTION

1. Field of the Invention

The present invention relates to a composition which is suitable for controlling fungal pests, comprising customary additives and an effective amount of a p-hydroxyaniline derivative of the general formula I $$\text{HO}-\underset{R^3}{\underset{|}{\bigcirc}}-\text{NH}-\overset{O}{\underset{\|}{C}}-R^1 \qquad \text{I}$$

where the radicals have the following meanings:

$R^1$ is hydrogen, $C_1$–$C_8$-alkyl which can be partially or fully halogenated and/or can have attached to it one or two of the following groups: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl, it being possible for the cyclic groups, in turn, to have attached to them one to three halogen atoms, $C_1$–$C_3$-alkyl groups and/or $C_1$–$C_3$-alkoxy groups, and aryl which can be partially or fully halogenated and/or can have attached to it one to three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, $C_6$–$C_{15}$-bicycloalkyl or $C_7$–$C_{15}$-bicycloalkenyl, it being possible for these radicals to be partially or fully halogenated and/or to have attached to them one to five of the following groups: $C_1$–$C_4$-alkyl, $C_1$–$C_4$-haloalkyl, $C_1$–$C_4$-alkoxy, $C_1$–$C_4$-haloalkoxy and aryl which can be partially or fully halogenated and/or can have attached to it one to three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ and $R^3$ independently of one another are halogen, $C_1$–$C_4$-alkyl, $C_1$–$C_4$-haloalkyl, $C_1$–$C_4$-alkoxy or $C_1$–$C_4$-haloalkoxy.

The invention furthermore relates to the use of the compounds I and of the compositions comprising them for controlling fungal pests, and to the use of the compounds I for the preparation of the compositions.

2. Description of the Background

The literature discloses alkylcarboxanilides which are fungicidally active (U.S. Pat. No. 3,849,478, U.S. Pat. No. 3,958,006, EP-A 293 718 and JP-A 345 751/93).

EP-A 339 418 furthermore discloses 4-hydroxyanilides, but these are not yet satisfactory with regard to their fungicidal action.

SUMMARY OF THE INVENTION

It was an object of the present invention to provide compositions which have an improved action against a wider spectrum of fungal pests.

Accordingly, we have found that this object is achieved by the compositions defined at the outset.

We have also found the use of these compositions and of the compounds I for controlling fungal pests and the use of the compounds I for the preparation of the compositions.

DETAILED DESCRIPTION OF THE INVENTION

EP-A 653 417 and EP-A 653 418 disclose the compounds of the general formula I and their preparation. In these documents, the compounds are described as intermediates for fungicidal o-acylated p-hydroxyaniline derivatives.

The hydroxyaniline derivatives of the general formula I are obtained by reacting a p-hydroxyaniline of the formula II in a manner known per se (cf. DE-A 32 02 100; EP-A 339 418) with a carbonyl derivative of the formula III in an inert organic solvent in the presence or absence of a base.

$$\text{HO}-\underset{R^3}{\underset{|}{\bigcirc}}-\text{NH}_2 + X-\overset{O}{\underset{\|}{C}}-R^1 \longrightarrow$$
$$\text{II} \qquad \text{III}$$

$$\text{HO}-\underset{R^3}{\underset{|}{\bigcirc}}-\text{NH}-\overset{O}{\underset{\|}{C}}-R^1$$
$$\text{I}$$

In formula III, the variable X is halogen, in particular chlorine, bromine and iodine, or a leaving group customary in acylation reactions, eg. $R^1$—CO—O.

The reaction is conventionally carried out at from −70 to 140, preferably 0 to 110, °C.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide and dimethylformamide.

Mixtures of these can also be used.

Preferred solvents are dioxane, tetrahydrofuran and dimethylformamide, either alone or as a mixture.

Suitable bases are: alkali metal and alkaline earth metal hydroxides, eg. lithium hydroxide, sodium hydroxide, potassium hydroxide, calcium hydroxide; alkali metal and alkaline earth metal oxides, eg. lithium oxide, sodium oxide, calcium oxide, magnesium oxide; alkali metal amides, eg. lithium amide, sodium amide, potassium amide; alkali metal and alkaline earth metal carbonates, eg. lithium carbonate, calcium carbonate; alkali metal hydrogen carbonates, eg. sodium hydrogen carbonate; alkali metal and alkaline earth metal alcoholates, eg. sodium methanolate, sodium ethanolate, potassium ethanolate, potassium tert-butanolate, dimethoxymagnesium; organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines.

Bases which are particularly preferably used are alkali metal carbonates, alkali metal alcoholates or tertiary amines.

The bases are generally employed in equimolar amounts, but they can also be used in an excess or as a solvent.

The educts are generally reacted with each other in equimolar amounts. It may be advantageous for the yield to employ the carbonyl derivative III in an excess or substoichiometric amount based on the p-hydroxyaniline II.

Those starting materials II and III required for the reaction which are not already known from the literature (II: J. Chem. Soc. part I, 1, 1 (1973); Houben-Weyl, Vol. 10/1, pp. 1140; ibid. Vol. 6/1c, pp. 85–101; III: Houben-Weyl, E5, Part 1, p. 587; Can. J. Chem. 71, pp. 1099–1105 (1993)) can be prepared in accordance with the literature cited.

The reaction mixtures are worked up in the customary manner, eg. by mixing with water, separation of the phases and, if desired, chromatographic purification of the crude products. Some of the products are obtained in the form of colorless or pale brown, viscous oils which can be freed or purified from volatile components under reduced pressure and at moderately elevated temperature. If the intermediates and end products are obtained as solids, they can also be purified by recrystallization or digestion.

The compounds I can contain one or more asymmetric centers and are obtained by the processes described in the form of enantiomer or diastereomer mixtures. The ratios by weight can differ as a function of the groups. If desired, these mixtures can be separated by customary methods. The compounds I can be used as pure isomers or else in the form of isomer mixtures.

In the definitions of the compounds I given at the outset, collective terms were used which generally represent the following substituents:

halogen: fluorine, chlorine, bromine and iodine;

alkyl: straight-chain or branched alkyl groups having 1 to 3, 4, 6 or 8 carbon atoms, eg. $C_1$–$C_6$-alkyl, such as methyl, ethyl, propyl, 1-methylethyl, butyl, 1-methylpropyl, 2-methylpropyl, 1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl, or partially or fully halogenated alkyl: straight-chain or branched alkyl groups having 1 to 4, 6 or 8 carbon atoms, as mentioned above, it being possible for some or all of the hydrogen atoms in these groups to be replaced by halogen atoms, as mentioned above, eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkoxy groups having 1 to 3 or 4 carbon atoms, such as methyloxy, ethyloxy, propyloxy, 1-methylethyloxy, butyloxy, 1-methylpropyloxy, 2-methylpropyloxy and 1,1-dimethylethyloxy;

haloalkoxy: straight-chain or branched partially or fully halogenated alkyl groups having 1 to 4 carbon atoms, as mentioned above, these groups being bonded to the skeleton via an oxygen atom (—O—);

alkylthio: straight-chain or branched alkyl groups having 1 to 4 carbon atoms, as mentioned above, which are bonded to the skeleton via a sulfur atom (—S—);

cycloalkyl: monocyclic alkyl groups having 3 to 7 carbon ring members: cyclopropyl, cyclobutyl, cyclopentyl, cyclohexyl and cycloheptyl;

cycloalkenyl: monocyclic alkenyl groups having 5 to 7 carbon ring members and one or two double bonds: 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl;

bicycloalkyl: bicyclic alkyl groups having 6 to 15 carbon ring members, eg. bicyclo[2.1.1]hex-5-yl, bicyclo [2.2.1]hept-2-yl, bicyclo[2.2.2]oct-2-yl, bicyclo[3.2.1] oct-6-yl, bicyclo[3.2.2]non-6-yl, bicyclo[4.2.2]dec-7-yl, bicyclo[3.1.0]hex-1-yl, bicyclo[4.1.0]hept-1-yl, bicyclo[4.3.0]non-1-yl, bicyclo[4.4.0]dec-1-yl, particularly preferably 5-methylbicyclo[2.1.1]hex-5-yl, 2-methylbicyclo[2.2.1]hept-2-yl, 2-methylbicyclo [2.2.2]oct-2-yl, 6-methylbicyclo[3.2.1]oct-6-yl, 6-methylbicyclo[3.2.2]non-6-yl, 7-methylbicyclo [4.2.2]dec-7-yl, 1-methylbicyclo[3.1.0]hex-1-yl, 1-methylbicyclo[4.1.0]hept-1-yl, 1-methylbicyclo [4.3.0]non-1-yl, 1-methylbicyclo[4.4.0]dec-1-yl, 2-methylbicyclo[3.1.0]hex-1-yl, 2-methylbicyclo [4.1.0]hept-1-yl, 2-methylbicyclo[4.3.0]non-1-yl, 2-methylbicyclo[4.4.0]dec-1-yl;

bicycloalkenyl: bicyclic alkenyl groups having 7 to 15 carbon ring members, eg. bicyclo[2.2.1]hept-2-en-5-yl, bicyclo[2.2.2]oct-2-en-5-yl, bicyclo[4.2.2]dec-7-en-2-yl, bicyclo[4.3.0]non-7-en-1-yl, bicyclo[4.4.0]dec-3-en-1-yl, bicyclo[4.1.0]hept-3-en-1-yl, 5-methylbicyclo [2.2.1)-hept-2-en-5-yl, 5-methylbicyclo[2.2.2]oct-2-en-5-yl, 2-methylbicyclo[4.2.2]dec-7-en-2-yl, 2-methylbicyclo[4.3.0]-non-7-en-1-yl, 2-methylbicyclo[4.4.0]dec-3-en-1-yl, 2-methylbicyclo [4.1.0]hept-3-en-1-yl;

aryl: phenyl or naphthyl.

The term "partially or fully halogenated" is to be understood as meaning that some or all of the hydrogen atoms in the groups thus characterized can be replaced by identical or different halogen atoms, as mentioned above.

Preferred compounds of the formula I with regard to their biological action against fungal pests are those where $R^1$ is an alkyl group substituted or branched in the 1-position, preferred substituents being: halogen, $C_1$–$C_4$-alkoxy and aryl which can be partially or fully halogenated and/or can have attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, where $R^1$ is 2-methylbicyclo[2.2.1]hept-2-yl, 2-methylbicyclo[2.2.2]oct-2-yl, bicyclo[4.1.0]hept-1-yl, 1-methylbicyclo[4.3.0]non-1-yl, 1-methylbicyclo [4.4.0]-dec-1-yl, 1-methylbicyclo[4.1.0]hept-1-yl, 2-methyl-bicyclo[4.3.0]non-1-yl, 2-methylbicyclo [4.4.0]dec-1-yl, 5-methylbicyclo[2.2.1]hept-2-yl, 5-methylbicyclo[2.2.2]-oct-2-en-5-yl, 2-methylbicyclo [4.4.0]dec-3-en-1-yl, or 2-methylbicyclo[4.1.0]hept-3-en-1-yl, where $R^2$ is halogen, alkyl or alkoxy, where $R^2$ is alkyl, in particular methyl, where $R^2$ is fluorine or chlorine, where $R^3$ is alkyl, haloalkyl, alkoxy or haloalkoxy, where $R^3$ is halogen, alkyl, haloalkyl or haloalkoxy and/or where $R^3$ is fluorine, chlorine, methyl or trifluoromethyl.

Other particularly preferred compounds I are those where $R^1$ is 1,1-dimethylethyl, 1,1-dimethylpropyl, 1-methyl-1-ethylpropyl, 2-chloro-1,1-dimethylethyl and 2-fluoro-1,1-dimethylethyl.

Very particularly preferred with regard to their use for controlling fungal pests are the compounds compiled in Tables 1 to 18 below.

TABLE 1

Compounds of the general formula I.1 where the combination of the substituents $R^2$ and $R^3$ is a compound of in each case one line of Table A

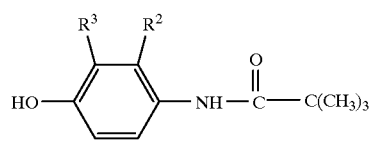

I.1

TABLE 2

Compounds of the general formula I.2 where the combination of the substituents $R^2$ and $R^3$ is a compound of in each case one line of Table A

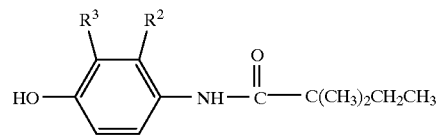

I.2

TABLE 3

Compounds of the general formula I.3 where the combination of the substituents $R^2$ and $R^3$ is a compound of in each case one line of Table A

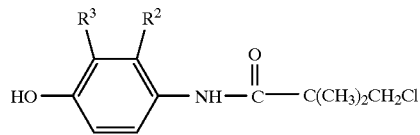

I.3

TABLE 4

Compounds of the general formula I.4 where the combination of the substituents $R^2$ and $R^3$ is a compound of in each case one line of Table A

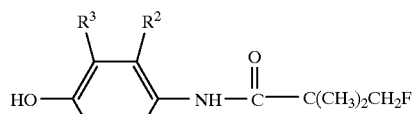

I.4

TABLE 5

Compounds of the general formula I.5 where the combination of the substituents $R^2$ and $R^3$ is a compound of in each case one line of Table A

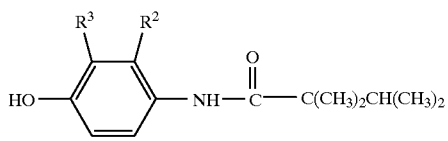

I.5

TABLE 6

Compounds of the general formula I.6 where the combination of the substituents $R^2$ and $R^3$ is a compound of in each case one line of Table A

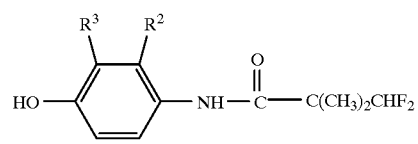

I.6

TABLE 7

Compounds of the general formula I.7 where the combination of the substituents $R^2$ and $R^3$ is a compound of in each case one line of Table A

I.7

TABLE 8

Compounds of the general formula I.8 where the combination of the substituents $R^2$ and $R^3$ is a compound of in each case one line of Table A

I.8

TABLE 9

Compounds of the general formula I.9 where the combination of the substituents $R^2$ and $R^3$ is a compound of in each case one line of Table A

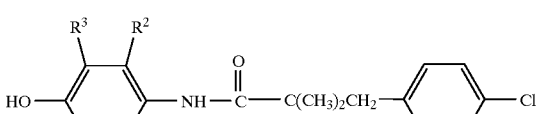

I.9

TABLE 10

Compounds of the general formula I.10 where the combination of the substituents $R^2$ and $R^3$ is a compound of in each case one line of Table A

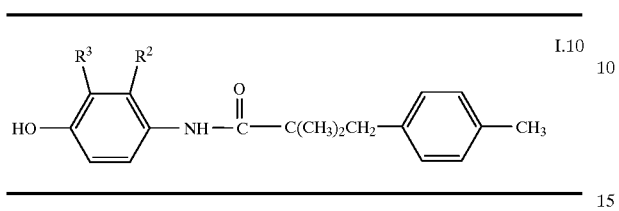

I.10

TABLE 11

Compounds of the general formula I.11 where the combination of the substituents $R^2$ and $R^3$ is a compound of in each case one line of Table A

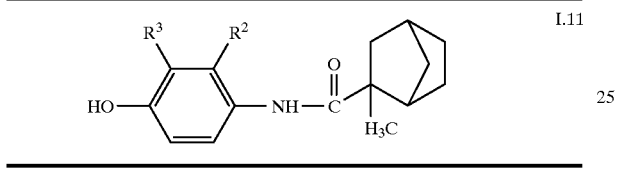

I.11

TABLE 12

Compounds of the general formula I.12 where the combination of the substituents $R^2$ and $R^3$ is a compound of in each case one line of Table A

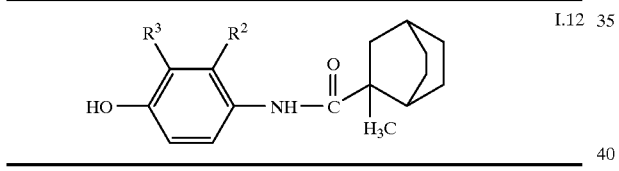

I.12

TABLE 13

Compounds of the general formula I.13 where the combination of the substituents $R^2$ and $R^3$ is a compound of in each case one line of Table A

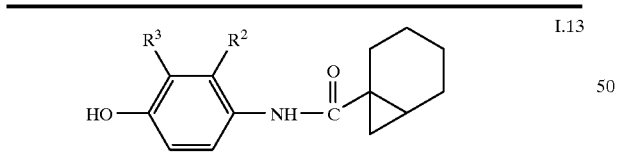

I.13

TABLE 14

Compounds of the general formula I.14 where the combination of the substituents $R^2$ and $R^3$ is a compound of in each case one line of Table A

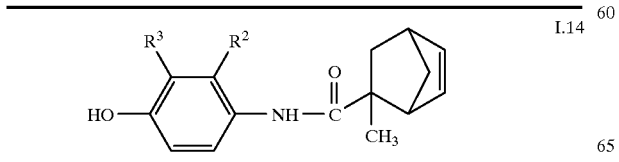

I.14

TABLE 15

Compounds of the general formula I.15 where the combination of the substituents $R^2$ and $R^3$ is a compound of in each case one line of Table A

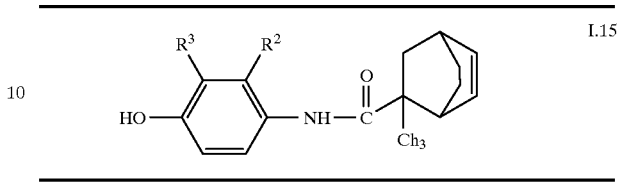

I.15

TABLE 16

Compounds of the general formula I.16 where the combination of the substituents $R^2$ and $R^3$ is a compound of in each case one line of Table A

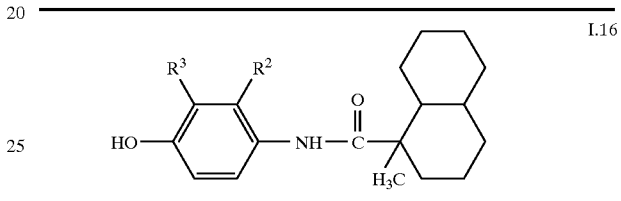

I.16

TABLE 17

Compounds of the general formula I.17 where the combination of the substituents $R^2$ and $R^3$ is a compound of in each case one line of Table A

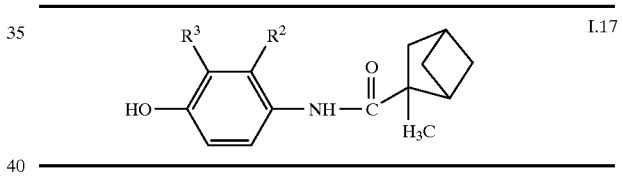

I.17

TABLE 18

Compounds of the general formula I.18 where the combination of the substituents $R^2$ and $R^3$ is a compound of in each case one line of Table A

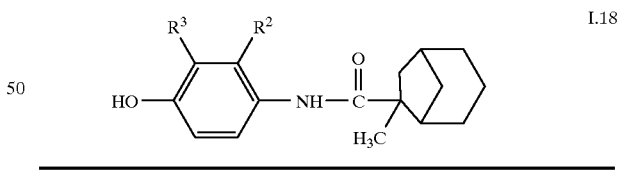

I.18

TABLE A

| No. | $R^2$ | $R^3$ |
|---|---|---|
| 1 | Cl | Cl |
| 2 | Cl | $CH_3$ |
| 3 | $CH_3$ | Cl |
| 4 | F | F |
| 5 | F | $CH_3$ |
| 6 | $CH_3$ | F |
| 7 | Cl | F |
| 8 | F | Cl |
| 9 | $CH_3$ | $CH_3$ |

The novel compounds of the formula I are useful as fungicides.

The novel compounds, or the compositions comprising them, can be used, for example, in the form of ready-to-spray solutions, powders, suspensions, also high-percentage aqueous, oily or other suspensions, or dispersions, emulsions, oil dispersions, pastes, dusts, materials for spreading or granules, by means of spraying, atomizing, dusting, spreading or pouring. The use forms depend on the intended aims; in any case, they should guarantee the finest possible distribution of the active ingredients according to the invention.

Normally, the plants are sprayed or dusted with the active ingredients, or the seeds of the plants are treated with the active ingredients.

The formulations are prepared in a known manner, eg. by extending the active ingredient with solvents and/or carriers, if desired using emulsifiers and dispersants, it also being possible to use other organic solvents as auxiliary solvents if water is used as diluent. Suitable auxiliaries are essentially: solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers, such as ground natural minerals (eg. kaolins, clays, talc, chalk) and ground synthetic minerals (eg. highly-disperse silica, silicates), emulsifiers, such as non-ionic and anionic emulsifiers (eg. polyoxyethylene fatty alcohol ethers, alkylsulfonates and arylsulfonates) and dispersants, such as lignosulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and of its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders, or other solid carriers.

Examples of such preparations are (the active ingredients used are termed in accordance with Table B):

I. a solution of 90 parts by weight of the compound No. 1 and 10 parts by weight of N-methyl-α-pyrrolidone which is suitable for use in the form of microdrops;

II. a mixture of 20 parts by weight of the compound No. 1, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water.

III. an aqueous dispersion of 20 parts by weight of the compound No. 1, 40 parts by weight of cyclohexanone, 30 parts by weight of isobutanol, 20 parts by weight of the adduct of 40 mol of ethylene oxide to 1 mol of castor oil;

IV. an aqueous dispersion of 20 parts by weight of the compound No. 2, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of the compound No. 2, 3 parts by weight of sodium diisobutylnaphthalene-α-sulfonate, 10 parts by weight of a sodium lignosulfonate from a sulfite waste liquor and 7 parts by weight of pulverulent silica gel; a spray mixture is obtained by finely distributing the mixture in water;

VI. an intimate mixture of 3 parts by weight of the compound No. 2 and 97 parts by weight of finely divided kaolin; this dust comprises 3% by weight of active ingredient;

VII. an intimate mixture of 30 parts by weight of the compound No. 3, 92 parts by weight of pulverulent silica gel and 8 parts by weight of paraffin oil which has been sprayed onto the surface of this silica gel; this preparation imparts good adhesion properties to the active ingredient;

VIII. a stable aqueous dispersion of 40 parts by weight of the compound No. 3, 10 parts by weight of the sodium salt of a phenolsulfonic acid/urea/formaldehyde condensate, 2 parts by weight of silica gel and 48 parts by weight of water, which can be diluted further;

IX. a stable oily dispersion of 20 parts by weight of the compound No. 3, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

The compounds I and the compositions according to the invention are distinguished by an outstanding activity against a broad spectrum of phytopathogenic fungi, in particular from the classes of the Ascomycetes, Basidiomycetes, Deuteromycetes and Phycomycetes. Some of them act systemically and can be employed as foliar- and soil-acting fungicides.

They are particlarly important for the control of a large number of fungi on a variety of crop plants, such as wheat, rye, barley, oats, rice, maize, grass, cotton, soya, coffee, sugar cane, grape vine, fruit-bearing species, ornamentals and vegetables, such as cucumbers, beans and cucurbits, and on the seeds of these plants.

The compounds I and the compositions according to the invention are applied by treating the fungal pests, their environment or the seed, plants, areas, materials or spaces to be protected against fungal infection with a fungicidally active amount of the active ingredients I or of the compositions.

They are applied before or after infection of the seed, materials or plants with the fungi.

Specifically, the compounds I and the compositions according to the invention are suitable for controlling the following plant diseases:

*Erysiphe graminis* (powdery mildew) in cereals, *Erysiphe cichoracearum* and *Sphaerotheca fuliginea* in cucurbits, *Podosphaera leucotricha* in apples, Uncinula necator in grape vine, Puccinia species in cereals, Rhizoctonia species in cotton and lawn, Ustilago species in cereals and sugar cane, *Venturia inaequalis* (scab) in apples, Helminthosporium species in cereals, *Septoria nodorum* in wheat, *Botrytis cinerea* (gray mold) in strawberries, grape vine, ornamentals and vegetables, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grape vine and Alternaria species in vegetables and fruit.

Particularly preferred is the control of Botrytis by means of the compounds I or the compositions according to the invention.

The compounds I and the compositions according to the invention can also be employed in the protection of materials (protection of wood), eg. against *Paecilomyces variotii*.

In general, the compositions according to the invention comprise of from 0.1 to 95, preferably from 0.5 to 90, % by weight of active ingredient.

Depending on the nature of the desired effect, the rates of application are between 0.01 and 2.0 kg of active ingredient per ha.

In the treatment of seed, amounts of 0.001 to 50 g, preferably 0.01 to 10 g, of active ingredient are generally required per kilogram of seed.

The compositions according to the invention can also be present together with other active ingredients, eg. herbicides, insecticides, growth regulators and fungicides, or else with fertilizers.

In many cases, mixing them with other fungicides results in a widened fungicidal spectrum of action.

The following list of fungicidally active ingredients together with which the compounds according to the invention can be used is intended to illustrate possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide; nitro derivatives, such as dinitro-(1-methylheptyl)phenyl crotonate, 2-sec-butyl-4,6-dinitrophenyl-3,3-dimethylacrylate, 2-sec-butyl-4, 6-dinitrophenyl isopropyl carbonate, di-isopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo-[4,5-b]-quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1, 2,3-thiadiazole, 2-thiocyanomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethyl-morpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2, 4-triazole, 1-[2-(2,4-dichlorophenyl)-4-n-propyl-1,3-dioxolan-2-ylethyl]-1H-1,2,4-triazole, N-(n-propyl)-N-(2,4,6-trichloro-phenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinylmethanol, 5-butyl-2-dimethylamino-4-hydroxy-6-methylpyrimidine, bis(p-chlorophenyl)-3-pyridinylmethanol, 1,2-bis(3-ethoxycarbonyl-2-thioureido)benzene, 1,2-bis(3-methoxycarbonyl-2-thioureido)benzene, [2-(4-chloro-phenyl)ethyl]-(1,1-dimethylethyl)-1H-1,2,4-triazol-1-ylethanol, and various fungicides, such as dodecylguanidine acetate, 3-[3-(3,5-dimethyl-2-oxycyclohexyl)-2-hydroxyethyl)]glutarimide, hexachlorobenzene, methyl N-(2,6-dimethylphenyl)-N-(2-furoyl)-DL-alaninate, methyl N-(2, 6-dimethylphenyl)-N-(2'-methoxyacetyl)-DL-alaninate, N-(2,6-dimethylphenyl)-N-chloroacetyl-D,L-2-amino-butyrolactone, methyl N-(2,6-dimethylphenyl)-N-(phenylacetyl)-DL-alaninate, 5-methyl-5-vinyl-3-(3,5-dichlorophenyl)-2,4-dioxo-1,3-oxazolidine, 3-[3,5-dichlorophenyl(5-methyl-5-methoxy-methyl)]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethyl-(aminocarbonyl)-2-methoximino]acetamide, 1-[2-(2,4-dichloro-phenyl) pentyl]-1H-1,2,4-triazole, 2,4-difluoro-α-(1H-1,2,4-triazolyl-1-methyl)benzhydryl alcohol, N-(3-chloro-2, 6-dinitro-4-trifluoromethylphenyl)-5-trifluoromethyl-3-chloro-2-aminopyridine, 1-((bis(4-fluorophenyl) methylsilyl)-methyl)-1H-1,2,4-triazole, strobilurins, such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoximino-[α-(2- phenoxyphenyl)]acetamide, N-methyl-E-methoximino-α-(2,5-dimethylphenoxy)-o-tolyl] acetamide, anilinopyrimidines, such as N-(4,6-dimethylpyrimidin-2-yl)aniline, N-[4-methyl-6-(1-propinyl)pyrimidin-2-yl]aniline, N-(4-methyl-6-cyclopropylpyrimidin-2-yl)aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)-acryloylmorpholine, (2RS,3SR)-1-[3-(2-chlorophenyl)-2,3-epoxy-2-(4-fluorophenyl) propyl]-1H-1,2,4-triazole.

Synthesis Example

The protocol given in the Synthesis Example below, for the preparation of the compounds Ia, can be used for obtaining further representatives of the compounds I by modifying the starting compounds. Examples prepared accordingly are given in Table B below together with their physical data.

N-(2,3-dichloro-4-hydroxyphenyl)-3-chloro-2,2-dimethylpropane-carboxamide (Compound 1 in Table B)

1.55 g (0.01 mol) of chloropivaloyl chloride were added dropwise at 0° C. to a solution of 1.93 g (0.011 mol) of 4-amino-2,3-dichlorophenol in 30 ml of tetrahydrofuran, and stirring of the mixture was continued at 25° C. until starting compound was no longer detectable by thin-layer chromatography. The reaction mixture was subsequently poured into water and extracted three times using 20 ml of methylene chloride. The combined organic phases were washed twice using water, dried and concentrated. The residue was chroamtographed on silica gel (eluent: cyclohexane: ethyl acetate=2:1; yield: 0.75 g, m.p. 115° C.).

TABLE B

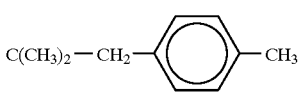

| No. | $R^3$ | $R^2$ | Q | M.p [° C.] |
|---|---|---|---|---|
| 1 | Cl | Cl | $C(CH_3)_2$—$CH_2$—Cl | 115 |
| 2 | Cl | Cl | $C(CH_3)_2$—$CH_2$—⌬—$CH_3$ | 110 |
| 3 | Cl | Cl | 2-$CH_3$-[2.2.1]-heptan-2-yl | 134 |
| 4 | F | $CH_3$ | $C(CH_3)_2$—$CH_3$ | 175 |
| 5 | F | $CH_3$ | $C(CH_3)_2$—$CH_2$—Cl | 155–160 |
| 6 | Cl | Cl | $C(CH_3)_2$—$CH_2$—⌬—Cl | 177 |
| 7 | F | $CH_3$ | $C(CH_3)_2$—$CH_2$—⌬—Cl | 182–4 |

TABLE B-continued

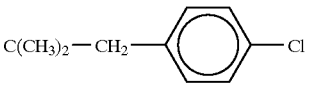

| No. | $R^3$ | $R^2$ | Q | M.p [° C.] |
|---|---|---|---|---|
| 8 | Cl | $CH_3$ | $C(CH_3)_2$—$CH_2CH_2CH_3$ | 165–9 |
| 9 | F | $CH_3$ | $C(CH_3)_2$—$CH_2CH_2CH_3$ | 135 |
| 10 | F | $CH_3$ | $C(CH_3)_2$—$CH_2Br$ | 170–3 |
| 11 | Cl | Cl | $C(CH_3)_2$—$CH_2CH_2CH_3$ | 155 |
| 12 | Cl | Cl | $C(CH_3)_2$—$CH_3$ | 158–162 |
| 13 | Cl | Cl | $C(CH_3)_2$—$CH_2Br$ | 133–8 |
| 14 | Cl | $CH_3$ | $C(CH_3)_2$—$CH_2Cl$ | 179 |
| 15 | Cl | $CH_3$ | $C(CH_3)_2$—$CH_2Br$ | 168 |
| 16 | Cl | $CH_3$ | $C(CH_3)_2$—$CH_3$ | 218 |
| 17 | Cl | $CH_3$ | $C(CH_3)_2$—$CH_2$—⌬—Cl | 207 |
| 18 | Cl | $CH_3$ | 2-$CH_3$-[2.2.1]-heptan-2-yl | 206–8 |
| 19 | Cl | Cl | 2-$CH_3$-[2.2.1]-heptan-2-yl | 135–7 |

Use Examples

In the following experiments on the fungicidal action of the compounds I, an emulsion was used whose composition was 10% by weight of the active ingredient and 90% by weight of a mixture of 70% by weight of cyclohexanol, 20% by weight of Nekanil® LN (Lutensol® AP6, wetting agent having an emulsifying and dispersant action based on ethoxylated alkylphenols) and 10% by weight of Emulphor® EL, (Emulan® EL, emulsifier based on ethoxylated fatty alcohols).

The desired concentrations of active ingredient were adjusted by diluting this emulsion with water.

Use Example I

Activity Against *Botrytis Cinerea*

After having formed 4 to 5 well-developed leaves, bell pepper seedlings cv. "Neusiedler Ideal Elite" were sprayed to run off point with aqueous suspensions which comprised 80% by weight of active ingredient and 20% by weight of emulsifier in the dry matter. After the spray coating had dried on, the plants were sprayed with a conidia suspension of the fungus *Botrytis cinerea* and placed in a chamber with high atmospheric humidity at 22–24° C. After 5 days, the disease on the untreated control plants had developed to such an extent that the foliar necroses formed extended to the predominant part of the leaves. The results were scored visually.

The experiment was carried out using in each case one of the following compounds of Table B: Nos. 1, 2, 3, 4, 5, 6, 7, 8, 9, 10, 11, 12, 13, 14, 15, 16, 17, 18.

When applying a preparation comprising 250 ppm of active ingredient, the fungal disease level expressed as a percentage of the leaf area was between 0 and 5%.

Untreated plants showed a disease level of 80%.

Use Example 2

Activity Against Powdery Mildew of Wheat

Leaves of wheat seedlings cv. "Frühgold" in pots were sprayed with aqueous spray mixture which comprised 80% by weight of active ingredient and 20% by weight of emulsifier in the dry matter, and, 24 hours after the spray coating had dried on, dusted with oidia (spores) of powdery mildew of wheat (*Erysiphe graminis* var. *tritici*). The test plants were then placed in the greenhouse at temperatures between 20 and 22° C. and a relative atmospheric humidity of 75 to 80%. After 7 days, the extent of mildew development was determined visually.

The experiment was carried out using in each case one of the following compounds of Table B: Nos. 1, 5, 6, 9, 10, 11, 13.

When applying a preparation comprising 250 ppm of active ingredient, the disease level, expressed as a percentage of the leaf area, was between 5 and 15%.

Untreated plants showed a disease level of 70%.

We claim:

1. A composition which is suitable for controlling fungal pests, comprising customary additives and an effective amount of a p-hydroxyaniline derivative of formula I

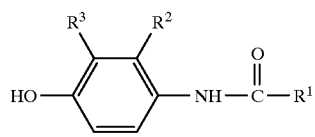

where the radicals have the following meanings:
 R$^1$ is a C$_6$–C$_{15}$-bicycloalkyl radical or a C$_7$–C$_{15}$-bicycloalkenyl radical, it being possible for these radicals to be partially or fully halogenated and/or to have attached to them one to five groups selected from the group consisting of C$_1$–C$_4$-alkyl, C$_1$–C$_4$-haloalkyl, C$_1$–C$_4$-alkoxy, C$_1$–C$_4$-haloalkoxy and aryl which can be partially or fully halogenated and/or can have attached to it one to three substituents selected from the group consisting of nitro, cyano, C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio;
 R$^2$ and R$^3$ independently of one another are halogen, C$_1$–C$_4$-alkyl, C$_1$–C$_4$-haloalkyl, C$_1$–C$_4$-alkoxy or C$_1$–C$_4$-haloalkoxy.

2. The composition of claim 1, wherein R$^1$ is said C$_6$–C$_{15}$-bicycloalkyl radical.

3. The composition of claim 1, wherein R$^1$ is said C$_7$–C$_{15}$-bicycloalkenyl radical.

4. The composition of claim 1, wherein R$^3$ is Cl or F.

5. The composition of claim 1, wherein R$^2$ is Cl or CH$_3$.

6. The composition of claim 1, wherein
 R$^3$ is Cl or F, and
 R$^2$ is Cl or CH$_3$.

7. The composition of claim 1, wherein R$^1$ is 2—CH$_3$—[2.2.1]-heptan-2-yl.

8. The composition of claim 6, wherein R$^1$ is 2—CH$_3$—[2.2.1]-heptan-2-yl.

9. A method of controlling fungal pests, which comprises treating the fungal pests, their environment, or the seed, plants, areas, materials or spaces to be kept free from them with an effective amount of a compound of the formula I as claimed in claim 1 or of a composition as claimed in claim 1.

10. A method as claimed in claim 9, which comprises carrying out the treatment with a compound I from the following table

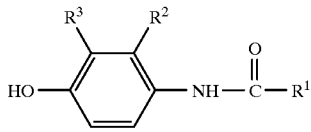

| No. | R$^3$ | R$^2$ | R$^1$ |
|---|---|---|---|
| 1 | Cl | Cl | C(CH$_3$)$_2$—CH$_2$-Cl |
| 2 | Cl | Cl | C(CH$_3$)$_2$—CH$_2$—C$_6$H$_4$—CH$_3$ |
| 3 | Cl | Cl | 2-CH$_3$-[2.2.1]-heptan-2-yl |
| 4 | F | CH$_3$ | C(CH$_3$)$_2$—CH$_3$ |
| 5 | F | CH$_3$ | C(CH$_3$)$_2$—CH$_2$—Cl |
| 6 | Cl | Cl | C(CH$_3$)$_2$—CH$_2$—C$_6$H$_4$—Cl |
| 7 | F | CH$_3$ | C(CH$_3$)$_2$—CH$_2$—C$_6$H$_4$—Cl |
| 8 | Cl | CH$_3$ | C(CH$_3$)$_2$—CH$_2$CH$_2$CH$_3$ |
| 9 | F | CH$_3$ | C(CH$_3$)$_2$—CH$_2$CH$_2$CH$_3$ |
| 10 | F | CH$_3$ | C(CH$_3$)$_2$—CH$_2$Br |
| 11 | Cl | Cl | C(CH$_3$)—CH$_2$CH$_2$CH$_3$ |
| 12 | Cl | Cl | C(CH$_3$)$_2$—CH$_3$ |
| 13 | Cl | Cl | C(CH$_3$)$_2$—CH$_2$Br |
| 14 | Cl | CH$_3$ | C(CH$_3$)$_2$—CH$_2$Cl |
| 15 | Cl | CH$_3$ | C(CH$_3$)$_2$—CH$_2$Br |
| 16 | Cl | CH$_3$ | C(CH$_3$)$_2$—CH$_3$ |
| 17 | Cl | CH$_3$ | C(CH$_3$)$_2$—CH$_2$—C$_6$H$_4$—Cl |
| 18 | Cl | CH$_3$ | 2-CH$_3$-[2.2.1]-heptan-2-yl |
| 19 | Cl | Cl | 2-CH$_3$-[2.2.1]-heptan-2-yl |

11. The method of claim 9, wherein said compound of formula I is used in said treating step.

12. The method of claim 9, wherein said composition is used in said treating step.

13. The method of claim 9, wherein R$^1$ is said C$_6$–C$_{15}$-bicycloalkyl radical.

14. The method of claim 9, wherein R$^1$ is said C$_7$–C$_{15}$-bicycloalkenyl radical.

15. The method of claim 9, wherein R$^3$ is Cl or F.

16. The method of claim 9, wherein R$^2$ is Cl or CH$_3$.

17. The method of claim 9, wherein
 R$^3$ is Cl or F, and
 R$^2$ is Cl or CH$_3$.

18. The method of claim 9, wherein R$^1$ is 2—CH$_3$—[2.2.1]-heptan-2-yl.

19. The method of claim 17, wherein R$^1$ is 2—CH$_3$—[2.2.1]-heptan-2-yl.

* * * * *